United States Patent [19]

O'Riordan et al.

[11] Patent Number: 5,378,227
[45] Date of Patent: Jan. 3, 1995

[54] BIOLOGICAL/PHARMACEUTICAL METHOD AND APPARATUS FOR COLLECTING AND MIXING FLUIDS

[75] Inventors: John F. O'Riordan, Arvada; Glen D. Antwiler, Lakewood, both of Colo.

[73] Assignee: Cobe Laboratories, Inc., Lakewood, Colo.

[21] Appl. No.: 928,040

[22] Filed: Aug. 11, 1992

[51] Int. Cl.$^6$ ............................................. A61M 5/00
[52] U.S. Cl. ........................................ 604/4; 604/19; 604/28
[58] Field of Search ................... 604/4, 19, 28, 30, 35, 604/65, 67, 118, 902

[56] References Cited

U.S. PATENT DOCUMENTS

| | | | |
|---|---|---|---|
| 3,851,181 | 11/1974 | Heule . | |
| 3,924,700 | 12/1975 | Lindsey et al. . | |
| 3,955,573 | 3/1976 | Hansen et al. . | |
| 3,964,484 | 6/1976 | Reynolds et al. . | |
| 3,965,896 | 6/1976 | Swank ............................... | 604/28 X |
| 4,000,972 | 1/1977 | Braun et al. . | |
| 4,002,170 | 1/1977 | Hansen et al. . | |
| 4,193,004 | 3/1980 | Lobdell et al. . | |
| 4,202,387 | 5/1980 | Upton . | |
| 4,231,366 | 11/1980 | Schael ............................... | 604/67 X |
| 4,253,456 | 3/1981 | Schindler et al. . | |
| 4,258,723 | 3/1981 | McCue et al. . | |
| 4,267,837 | 5/1981 | Purdy et al. . | |
| 4,275,726 | 6/1981 | Schael ............................... | 604/67 X |
| 4,370,983 | 2/1983 | Lichtenstein . | |
| 4,385,630 | 5/1983 | Gilcher ............................... | 604/35 X |
| 4,425,114 | 1/1984 | Schoendorfer et al. . | |
| 4,481,827 | 11/1984 | Bilstad et al. . | |
| 4,540,406 | 9/1985 | Miles . | |
| 4,551,131 | 11/1985 | Miles et al. . | |
| 4,592,743 | 6/1986 | Hjertman et al. . | |
| 4,598,733 | 7/1986 | Kanno et al. . | |
| 4,623,328 | 11/1986 | Hartranft . | |
| 4,658,834 | 4/1987 | Blankenship et al. . | |
| 4,769,001 | 9/1988 | Prince ............................... | 604/28 X |
| 4,850,998 | 7/1989 | Schoendorfer ..................... | 604/28 |
| 4,867,738 | 9/1989 | Mintz ................................. | 604/4 |
| 4,923,449 | 5/1990 | Toya et al. . | |
| 4,995,268 | 2/1991 | Ash et al. . | |
| 5,035,865 | 7/1991 | Inaba et al. . | |
| 5,055,198 | 10/1991 | Shettigar . | |
| 5,092,836 | 3/1992 | Polaschegg ........................ | 604/4 |
| 5,116,312 | 5/1992 | Blankenship et al. ............. | 604/66 |
| 5,141,493 | 8/1992 | Jacobsen et al. .................. | 604/28 X |

FOREIGN PATENT DOCUMENTS

| | | |
|---|---|---|
| 0208061A1 | 1/1987 | European Pat. Off. . |
| 0438703A1 | 7/1991 | European Pat. Off. . |
| 3739240A1 | 5/1988 | Germany . |
| 2009862A | 6/1979 | United Kingdom . |
| 2139094A | 11/1984 | United Kingdom . |
| WO88/06466 | 9/1988 | WIPO . |

OTHER PUBLICATIONS

European Search Report dated May 30, 1994 for application Serial No. 93306274.7.
Abstract of U.S. Patent No. 5,116,312.
"A Simple Autotransfusion System for Use in Abdominal Aortic Surgery," by A. Addison Barman et al., Surgical Rounds, Dec., 1987.
"Evaluation of a New Blood Autotransfusion Device," by John M. Toomasian et al., The Journal of Thoracic and Cardiovascular Surgery, vol. 92, No. 5, pp. 936–942, Nov., 1986.
Operating instructions for "Thoratec Bloodstat Autotransfusion System," Thoratec Laboratories Corporation, 1983.
510(k) Notification for "Thoratec Introperative Autotransfusion System," Thoratec Laboratories Corporation, Supplemental Submission, Jul. 25, 1983.

*Primary Examiner*—Sam Rimell
*Attorney, Agent, or Firm*—Finnegan, Henderson, Farabow, Garrett & Dunner

[57] ABSTRACT

A blood circulation apparatus includes a suction wand for receiving blood from a patient, a reservoir for collecting received blood, a conduit connecting the suction wand and the reservoir, an anticoagulant pump and line for introducing anticoagulant into the blood upstream of the reservoir, sensors for detecting liquid volume in the reservoir and for transmitting a corresponding volume signal, and a controller for regulating anticoagulant introduction in accordance with a predetermined program and as a function of the volume signal.

30 Claims, 3 Drawing Sheets

BIOLOGICAL/PHARMACEUTICAL METHOD AND APPARATUS FOR COLLECTING AND MIXING FLUIDS

BACKGROUND OF THE INVENTION

1. Field of the Invention

The invention relates generally to an apparatus and method for collecting and mixing two biological/pharmaceutical liquids. The invention may be used in connection with a method and apparatus for collecting whole blood from a donor and mixing the blood with anticoagulant fluids.

2. Description of the Related Art

During surgical procedures, blood is suctioned from surgical cavities using a suction wand that is connected to a blood reservoir for collecting the aspirated blood for later return to the patient. When handling blood in an extracorporeal device, blood readily tends to clot, making it unacceptable for reinfusion into a patient. Thus, it is often desirable to add an anticoagulant to the blood as it is aspirated. Typically, anticoagulant is added proximate the point of initial collection, such as through a side port of the suction wand or into a blood flow passageway adjacent to the suction wand.

In the conventional system, the suction wand is permanently in fluid communication with the blood reservoir where typically, in the case of a hard shell reservoir, a partial vacuum is created. When the suction wand is used, the infusion of anticoagulant is manually controlled by an operator.

If large influxes of blood are encountered during a procedure, it is up to the operator to recognize that additional anticoagulant is needed, and appropriately adjust the anticoagulant flow rate. In general, the operator will try to maintain a fixed ratio of anticoagulant to blood. The target ratio is usually predetermined based upon the anticoagulant being used and any other relevant data (e.g., the type of surgical procedure).

A drawback of this system is its inaccuracy. Because the flow rate and volumes of anticoagulant are manually controlled by the operator using a roller clamp on flexible tubing, the procedure has a high degree of variability. Not only are the initial settings inexact, they have a tendency to change with time caused by changes in the tubing, fluid height changes, and pressure changes in the system.

Another drawback of the related art system is that it does not fit the erratic occurrence and variable flow rate of blood losses, whereas each time the suction valve is used, varying amounts of anticoagulant are usually needed. For example, more anticoagulant is needed as the suction wand draws only blood than when the wand draws a combination of blood and air. However, with the conventional system, unless an operator intervenes, the same amount of anticoagulant is infused into the blood passageway regardless of the amount of blood being suctioned. Even if an operator intervenes, it is difficult to manually achieve a target ratio. Thus, with the conventional apparatus and method, it is possible to infuse too much or too little anticoagulant into the blood, which could lead to dangerous medical conditions.

SUMMARY OF THE INVENTION

An object of the present invention is to precisely control the infusion of a first liquid into a second liquid.

Another object of the present invention is to provide a method and apparatus that provides a preselected amount of anticoagulant to a blood collection system, the amount of anticoagulant infused being a function of a volume of blood in the collection system.

A further object of the present invention is to prevent an excess amount of anticoagulant from being infused into a blood collection system.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purposes of the invention, as embodied and broadly described herein, the apparatus of the invention comprises means for receiving blood from a patient, a reservoir for collecting received blood, a conduit connecting the receiving means and the reservoir, means for introducing anticoagulant into the received blood, means for sensing liquid volume in the reservoir and for transmitting a volume signal corresponding thereto, and control means for regulating the anticoagulant introducing means in accordance with a predetermined program and as a function of the volume signal.

In addition, the method of the invention comprises the steps of receiving blood from a patient, collecting the received blood in a reservoir, monitoring a liquid volume within the reservoir using a sensor, outputting a volume signal corresponding to a liquid volume sensed by the sensor, introducing anticoagulant into the blood, and controlling the introduction of anticoagulant in accordance with a predetermined program and as a function of the volume signal.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention, and together with the description, serve to explain the principles of the invention.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

Figure 1:
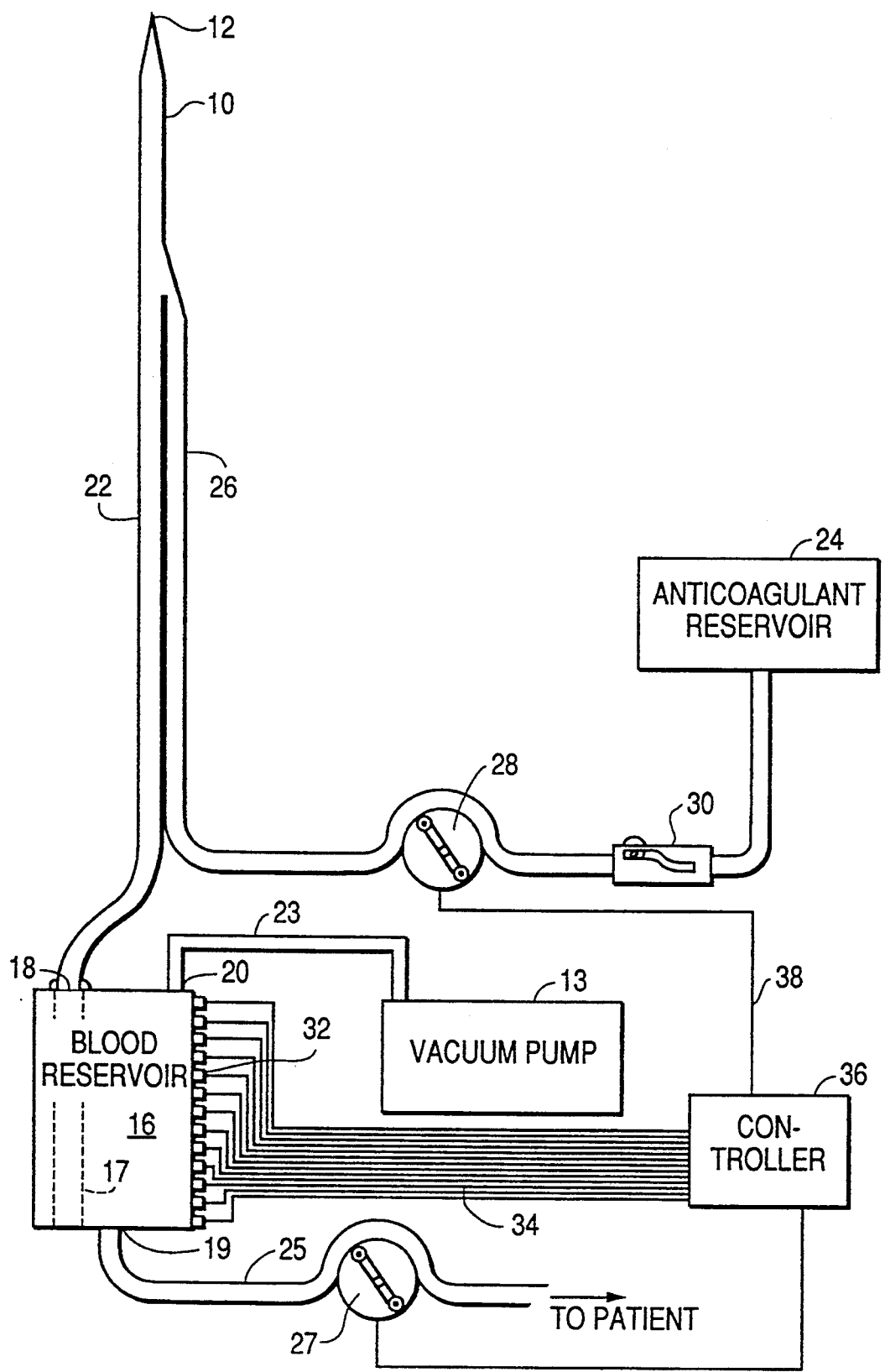
FIG. 1 is a schematic diagram of a blood collection apparatus in accordance with the present invention.

In accordance with the invention there is provided a blood collection apparatus including means for receiving blood from a patient. As embodied herein, and as illustrated in FIG. 1, the blood receiving means includes suction wand 10 such as those conventionally used to suction blood and other fluids from surgical cavities. Suction wand 10 includes an opened end 12 for suctioning blood.

In accordance with the invention there is also provided a reservoir for collecting received blood, and means for transporting received blood to the reservoir. As embodied herein, the transporting means includes tubing segment 22 which connects blood reservoir 16 with suction wand 10, and pump means such as a peristaltic pump or a vacuum pump for conveying fluid through tubing segment 22.

According to a first embodiment of the invention, the pump means includes vacuum pump 13, and blood reservoir 16 includes a hard outer shell constructed, for example, of plastic. As illustrated in FIG. 1, blood reservoir 16 also includes vacuum port 20, inlet port 18, and outlet port 19. Inlet port 18 is connected to tubing segment 22, vacuum port 20 is connected to vacuum pump 13 through tubing segment 23, and outlet port 19 is connected to tubing segment 25 for returning collected blood to the patient or conveying it to a blood treatment device. The tip end 12 of suction wand 10 is permanently in fluid communication with vacuum pump 13, whereby fluid can be suctioned through wand 10 and tubing segment 22 into blood reservoir 16. Similarly, in the embodiment of Fig 4, the pump means includes peristaltic pump 42, directly located in tubing segment 22 for pumping fluid from suction wand 10 into blood reservoir 16.

Blood reservoir 16 may also include a filter 17 extending from inlet port 18 along the interior length of the reservoir. Not only does filter 17 catch any blood clots that may have formed, but it also dampens fluid flow into the reservoir to prevent waves and splashes. Preferably a peristaltic pump 27 is provided in tubing segment 25 for emptying the blood reservoir 16, and returning the blood directly to the patient, or conveying it to a device for further processing.

While the preferred embodiments of the present invention are described in connection with the suctioning of blood from surgical cavities, the invention has broad medical applications. Even when used in the medical field, the invention is not limited to a suctioning apparatus, but may be used in other types of extracorporeal blood circuits and blood collection devices. For example, in certain applications, in lieu of the suction wand, the blood receiving means may include a blood collecting needle for receiving blood from the arterio-venous system of a patient.

Also in accordance with the invention there is provided means for introducing anticoagulant into the blood at a predetermined infusion rate. As embodied herein, the anticoagulant introducing means includes anticoagulant reservoir 24 connected to suction wand 10 via tubing segment 26. Anticoagulant reservoir 24 is typically used for holding a volume of anticoagulant such as heparin or citrate. A pump, such as a variable speed peristaltic pump 28, engages tubing segment 26 for pumping anticoagulant through tubing segment 26 and into tubing segment 22. In addition, a roller clamp 30 may be provided in tubing segment 26 to permit manual restriction of anticoagulant flow in the event of system failure. As is discussed later in greater detail, the speed of pump 28 is controlled to achieve a predetermined infusion rate for the anticoagulant.

Tubing segments 22 and 26 may be joined in a "Y" configuration adjacent suction wand 10. This structure permits anticoagulant to be added to the blood immediately as it is suctioned from a surgical cavity so that coagulation may be prevented as blood travels through tubing segment 22.

Figure 2:
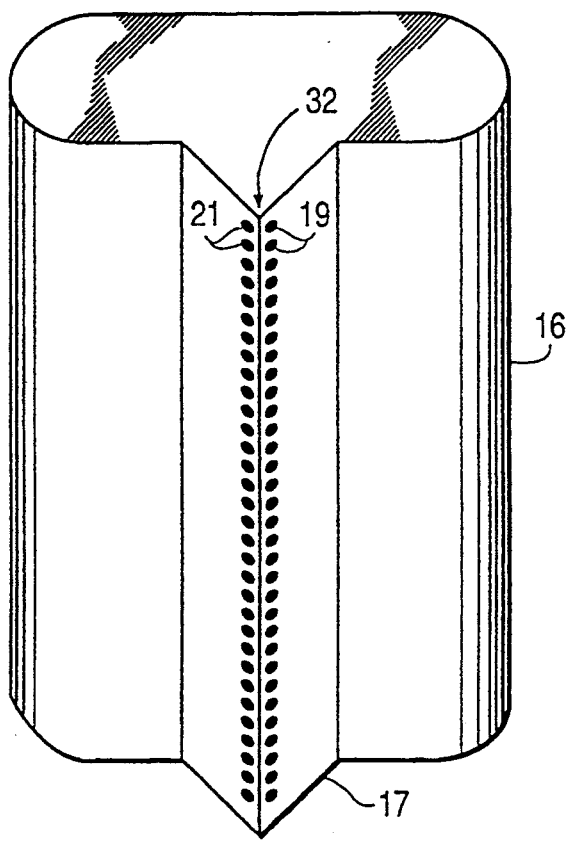
FIG. 2 is a perspective view of the blood reservoir depicted in FIG. 1.
Figure 3:
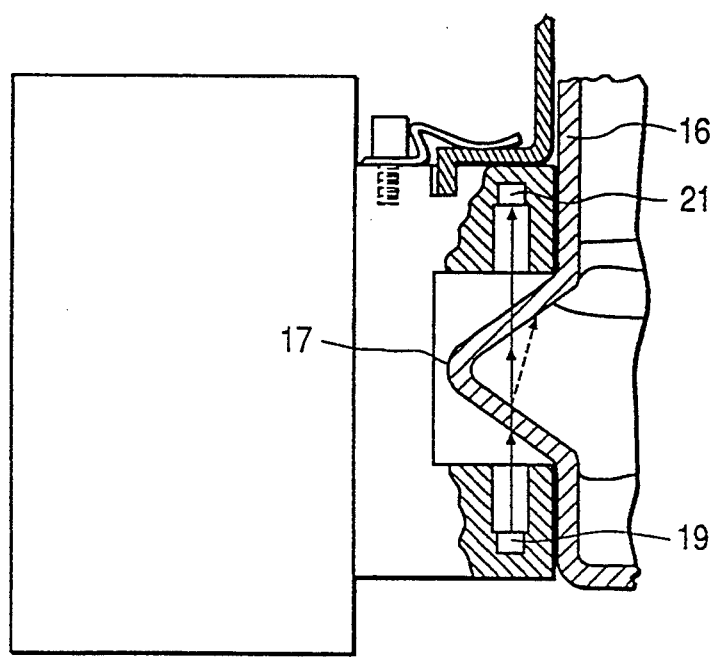
FIG. 3 is a fragmentary sectional view showing a detail of the blood reservoir depicted in FIG. 2.

In accordance with the present invention there is also provided means for sensing liquid volume in the reservoir and for transmitting a volume signal corresponding thereto. As embodied herein, and as best illustrated in FIGS. 2 and 3, the sensing means includes an array of optical detectors 32 extending vertically along blood reservoir 16. For example, optical detectors 32 may include a set of thirty-two pairs of light emitting diodes 19 and phototransistors 21. The detector pairs are arranged to sense the presence of fluid at their individual height. According to a preferred embodiment, the detector pairs are spaced from each other at 100 ml intervals. The bottom sensor is placed at a volume of 100 ml. Therefore, the volume in the reservoir can be detected within ±50 ml.

Reservoir 16, illustrated in FIG. 2, is substantially elliptical in cross-section and includes a V-shaped protrusion 17 extending in the vertical direction of the reservoir. Preferably, the walls of the V-shaped protrusion are oriented at a 90° angle to each other. The array of optical detectors 32 are arranged along V-shaped protrusion 17 so that each of the light emitting diodes 19 is oriented opposite a corresponding phototransistor 21. Liquid volume sensed by optical detectors 32 is converted into an electrical signal which is transmitted through one of signal lines 34.

In accordance with the invention there is provided control means for regulating the anticoagulant introducing means in accordance with a predetermined program and as a function of the volume signal. As embodied herein and as illustrated in FIG. 1, the control means includes controller 36 electrically connected to each of the array of optical detectors 32 through signal lines 34 for receiving the volume signal from the array. Controller 36 is also connected through signal line 38 to peristaltic pump 28, and includes a microprocessor that is programmed with an algorithm to automatically administer anticoagulant by regulating pump 28 in response to the level detected in blood reservoir 16. Preferably, the program of the microprocessor includes an algorithm which filters out "noise" which may occur when the reservoir is inadvertently bumped and waves move through the blood supply.

In a preferred embodiment, the blood reservoir has a capacity of approximately 3.2 liters with detectors spaced along the vertical direction of the reservoir at 100 ml intervals. The average salvage rate may be calculated at each occurrence of detection by any sensor, as follows:

$$Qb = (Vinc + Vpump - Vac)/\text{Time}$$

where
  Qb = average rate of blood salvage at the most recent sensor change,
  Vinc = change in volume in reservoir during sensor change, acceptable values are +100, −100, or 0 ml,
  Vpump = volume pumped out of reservoir since previous sensor change,
  Vac = volume of anticoagulant pumped into reservoir since previous sensor change, and
  Time = time elapsed from previous sensor change.

As previously indicated, Vinc is a function of the level detected by the array of sensors 32, and corresponds to the change in fluid height in the reservoir. Vpump and Vac are calculated as a function of the number of respective pump revolutions (pumps 27 and 28).

Between sensor changes it is possible to calculate the maximum (Qb max) and minimum (Qb min) average salvage rates that could occur. These values are given by:

$$Qb\ max = (V - Vpump - Vac)/\text{Time}$$

$$Qb\ min = (V - 100ml + Vpump - Vac)/\text{Time}$$

where Vpump, Vac, and Time have similar definitions as above except that they are for the time interval since the most recent change, and where V=100 ml if the most recent sensor change indicated that the reservoir level was increasing, and V=0 ml if the most recent sensor change indicated that the reservoir level was decreasing. Between sensor changes the current estimate of Qb is assumed to equal the last calculated value for Qb unless it exceeds one of the bounds as defined by Qb max or Qb min in which case Qb is set equal to that bound.

With the above-described system, anticoagulant can be automatically delivered as a function of either volume of blood salvaged or the salvage rate. Given that the current desired practice is to anticoagulate salvaged blood at a specific ratio, one part anticoagulant to R parts of salvaged blood, the pump in a preferred embodiment may be set to run at Qb divided by the ratio but not less than a predetermined drip rate. The ratio is also selected by the operator and can be changed as desired.

Figure 4:
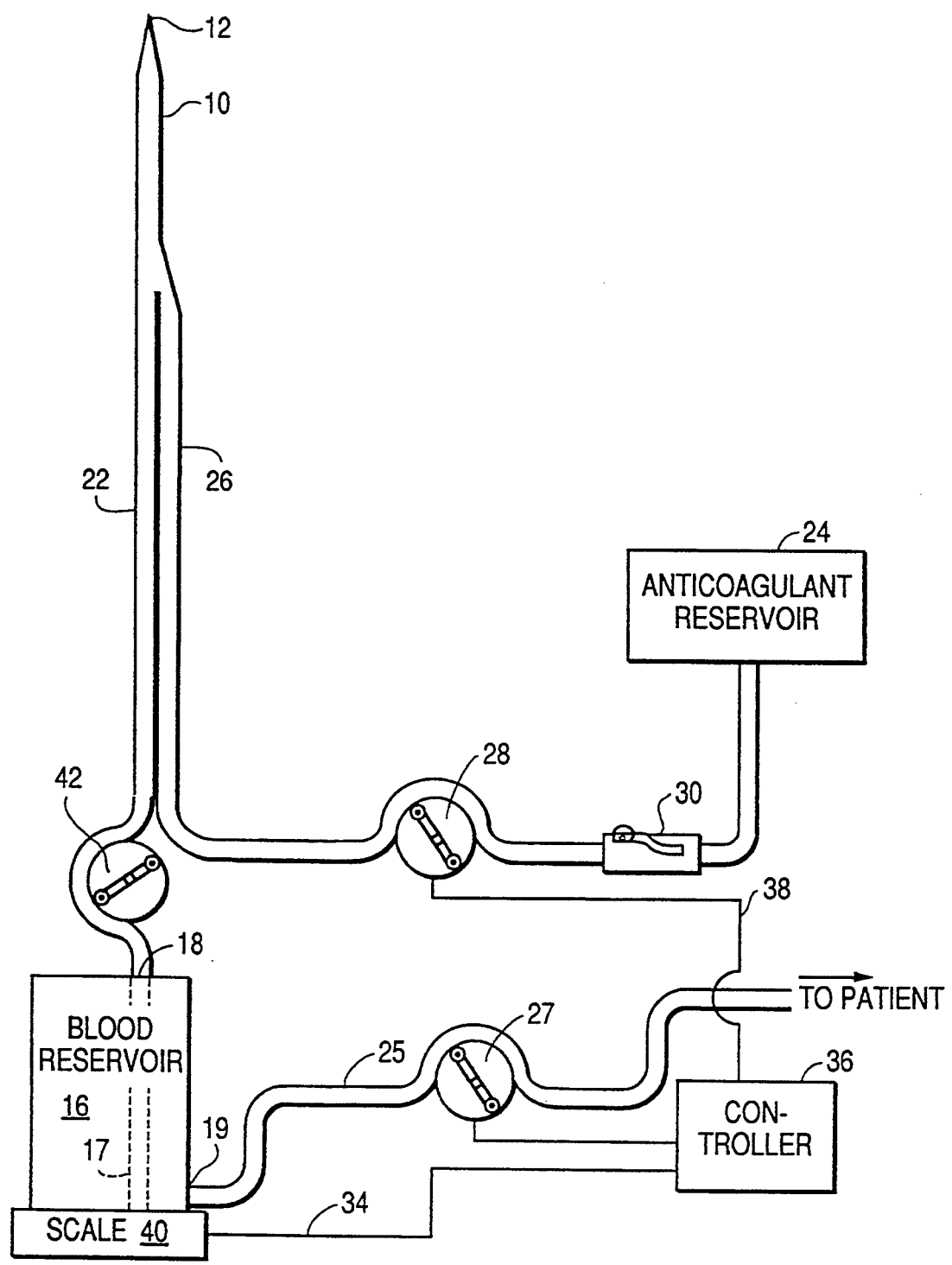
FIG. 4 is a schematic diagram of a second embodiment of the present invention.

An alternative preferred embodiment, depicted in FIG. 4, employs a scale 40 in lieu of an array of detectors for detecting blood volume in reservoir 16. An algorithm can be constructed by one skilled in the art to calculate the salvage rate and/or volume in the blood reservoir based upon known weights of anticoagulant and blood and the known volume of infused anticoagulant. In the embodiment of FIG. 4, since an array of detectors is not needed, blood reservoir 16 may include a conventional flexible plastic, blood bag. If a blood bag is used, a peristaltic pump 42 is located in tubing segment 22 as illustrated in FIG. 3, as a substitute for vacuum pump 13 (illustrated in FIG. 1) which would otherwise collapse a plastic blood bag in absence of an additional support. Pump 42 could also be used in connection with the embodiment of FIG. 1 in lieu of vacuum pump 13, if desired.

In both the first and second embodiments, the control means may also include input means, such as a keypad (not shown), for permitting an operator to select various parameters of anticoagulant infusion. For example, the input means may permit a user to set minimum pump speed, a target ratio, or may even permit manual control by completely overriding the programmed algorithm.

In another embodiment, (not illustrated) the receiving and transporting means may be a sponge that is used to absorb blood from the surgical cavity and is then manually squeezed into a basin from whence it is transferred into the blood reservoir. When the sensing means detects the increased volume in the reservoir, the control means directs an appropriate amount of anticoagulant directly into the blood reservoir.

Because the above-described embodiments regulate anticoagulant infusion using detected volume in the blood reservoir, they can handle any incoming flow rate while still providing a preselected ratio of anticoagulant to blood. In addition, since neither the detectors of the first embodiment nor the scale of the second embodiment detect air suctioned through suction wand 10, the invention works well regardless of whether large volumes of air are suctioned along with the blood. Finally, the invention permits an operator to select target ratios, and vary those target ratios depending upon the percentage of anticoagulant desired.

While the invention is described in connection with the infusion of anticoagulant into blood, the invention is not intended to be limited to such uses. For example, the invention has broad applications to other medical systems which will be apparent to those skilled in the art and which may be constructed without departing from the scope and spirit of the invention. Additionally, rather than using an array of optical detectors 32 or scale 40 to monitor accumulation of blood and anticoagulant in reservoir 16, a flow detector may be placed in tubing segment 22 to monitor the rate of flow into the reservoir. The monitored rate of flow and an appropriate clock for detecting the length of time the flow rates occur can be used to determine very accurately the amount of blood being suctioned, and the flow of anticoagulant can be infused in accordance therewith. Thus, it is intended that the specification and examples be considered as exemplary only, with a true scope and spirit of the invention being indicated by the following claims.

What is claimed is:

1. A blood collection apparatus, comprising:
   means for receiving blood from a patient;
   a reservoir for collecting received blood;
   means for transporting received blood from the receiving means to the reservoir;
   and means for preventing blood coagulation in reservoir, the preventing means including:
      means for introducing anticoagulant into the received blood at a predetermined infusion rate before the blood leaves the reservoir;
      means for sensing liquid volume in the reservoir and for transmitting a volume signal corresponding thereto; and
      control means for varying the predetermined infusion rate of the anticoagulant introducing means in accordance with a predetermined program and as a function of the volume signal.

2. An apparatus according to claim 1 wherein the receiving means includes a suction wand, and the transporting means includes pump means for drawing blood through the suction wand and a conduit flow connecting the suction wand and the reservoir.

3. An apparatus according to claim 2 wherein the pump means is a vacuum pump for establishing a negative pressure within the reservoir to induce flow into the reservoir.

4. An apparatus according to claim 2 wherein the pump means includes a peristaltic pump located between the receiving means and the reservoir.

5. An apparatus according to claim 1 wherein the reservoir is a hard shell container, and the sensing means includes a plurality of optical detectors arranged on the container.

6. An apparatus according to claim 1 wherein the anticoagulant introducing means includes an anticoagulant reservoir in fluid communication with the blood collecting reservoir.

7. An apparatus according to claim 6 wherein the anticoagulant introducing means further includes a variable speed pump, and wherein the control means regulates the speed of the pump as a function of the volume signal.

8. An apparatus according to claim 1 wherein the sensing means includes a scale for weighing the blood collecting reservoir.

9. An apparatus according to claim 1 further including input means for permitting a user to vary the predetermined program.

10. An apparatus according to claim 1 wherein the control means includes means for calculating a rate of volume change of fluid in the reservoir and means for regulating the flow of anticoagulant as a function of the calculated rate of volume change.

11. An apparatus according to claim 1 further including means for emptying the blood collecting reservoir, the predetermined infusion rate of the anticoagulant being further varied in accordance with the flow rate of the emptying of the blood collecting reservoir.

12. An apparatus according to claim 11 wherein the emptying means includes a pump.

13. An apparatus according to claim 1 wherein the control means regulates the anticoagulant infusion rate as a function of the average salvage rate Qb, defined by the formula Qb=(Vinc+Vpump−Vac)/time, wherein Vinc represents a change in reservoir volume, Vpump represents a fluid volume removed from the reservoir, and Vac represents a volume of anticoagulant added to the received blood.

14. An apparatus according to claim 13 wherein the control means maintains the infusion rate of the anticoagulant in proportion to the average salvage rate Qb.

15. An apparatus according to claim 13 wherein the control means maintains the infusion rate of anticoagulant above a predetermined minimum value regardless of the value of Qb.

16. A method for collecting blood from a patient, the method comprising the steps of:
receiving blood from a patient;
transporting the received blood to a reservoir;
and regulating a mixture ratio of anticoagulant and blood in the reservoir, the step of regulating including the substeps of:
monitoring a fluid volume within the reservoir using a sensor;
outputting a volume signal corresponding to the fluid volume in the reservoir as sensed by the sensor;
introducing anticoagulant into the received blood; and
controlling the introduction of anticoagulant in accordance with a predetermined program and as a function of the volume signal.

17. A method according to claim 16 wherein the step of receiving includes the substep of suctioning blood through a suction wand.

18. A method according to claim 16 wherein the step of transporting includes the substep of conveying blood from the receiving means to the reservoir using a pump.

19. A method according to claim 16 wherein the reservoir includes a series of optical detectors selectively positioned along the height of the reservoir, and the step of monitoring includes the substep of detecting, with the optical detectors, the volume of fluid in the reservoir.

20. A method according to claim 16 wherein the step of monitoring includes the substep of weighing the reservoir.

21. A method according to claim 16 wherein the step of introducing anticoagulant includes the substep of conveying anticoagulant into the received blood using a pump.

22. A method according to claim 16 wherein the step of controlling includes the substep of regulating a speed of the pump.

23. A method according to claim 16 where the predetermined program is variable in response to data supplied by a user.

24. A method according to claim 16 wherein the step of controlling includes the substep of calculating a rate of volume change of fluid in the reservoir and regulating anticoagulant flow as a function of the calculated rate change.

25. A method according to claim 16 wherein the infusion rate of the anticoagulant is varied as a function of the average salvage rate Qb, defined by the formula Qb=(Vinc+Vpump−Vac)/time, wherein Vinc represents a change in reservoir volume, Vpump represents a fluid volume removed from the reservoir, and Vac represents a volume of anticoagulant added to the received blood.

26. A method according to claim 25 wherein the infusion rate of the anticoagulant is proportional to the average salvage rate Qb.

27. A method according to claim 25 wherein the infusion rate of anticoagulant is maintained above a predetermined minimum value regardless of the value of Qb.

28. An apparatus for controlling flow of a medical fluid into flow of a biological fluid, the apparatus comprising:
a fluid reservoir;
transporting means for conveying the biological fluid into the fluid reservoir;
conduit means flow connected to the transporting means, for conveying the medical fluid into the transported biological fluid;
and means for regulating a mixture ratio of the medical fluid to the biological fluid in the reservoir, the regulating means including:
means for detecting volume in the fluid reservoir and for transmitting a corresponding volume signal; and
control means for varying said medical fluid flow as a function of said volume signal.

29. An apparatus according to claim 28, wherein the control means includes means for calculating a rate of volume change in the reservoir and regulating the medical fluid flow as a function of the calculated rate change.

30. A method for controlling flow of a medical fluid into flow of a biological fluid, the method comprising the steps of:
transporting the biological fluid to a reservoir;
monitoring a fluid volume within the reservoir using a sensor;
and regulating a mixture ratio of the medical fluid to the biological fluid in the reservoir, the step of regulating including the substeps of:
outputting a volume signal corresponding to a fluid volume sensed by the sensor;
introducing the medical fluid into the transported biological fluid; and
controlling the introduction of the medical fluid into the biological fluid as a function of the volume signal.

* * * * *